United States Patent [19]

Carr, Jr.

[11] Patent Number: 5,205,159

[45] Date of Patent: Apr. 27, 1993

[54] APPARATUS AND METHOD FOR MEASURING CLOT ELASTIC MODULUS AND FORCE DEVELOPMENT ON THE SAME BLOOD SAMPLE

[75] Inventor: Marcus E. Carr, Jr., Richmond, Va.

[73] Assignees: Virginia Commonwealth University, Richmond; Center for Innovative Technology, Herndon, both of Va.

[21] Appl. No.: 822,415

[22] Filed: Jan. 17, 1992

[51] Int. Cl.⁵ .......................................... G01N 33/48
[52] U.S. Cl. ..................... 73/64.41; 73/790; 73/822; 422/73
[58] Field of Search ............... 73/64.1, 760, 781, 788, 73/789, 790, 818, 822, 823; 422/73

[56] References Cited

U.S. PATENT DOCUMENTS 4,317,363  3/1982  Shen ..................................... 73/64.1
4,986,964  1/1991  Carr, Jr. et al. ..................... 422/73

OTHER PUBLICATIONS

Marcus E. Carr et al., Measurement of Platelet-Mediated Force, Am. J. of Med. Sci. 302:13-18 (1991).
Marcus E. Carr et al., Blood Coagulation and Fibrinolysis 2:303-308 (1991).
John D. Ferry et al., J. Am. Chem. Soc. 69:388-400 (1947).
John D. Ferry, Protein Gels, Adv. Protein Chem 4:1-78, (1948).
Marcus E. Carr et al., Analytical biochem. 72:202-211 (1976).
John D. Ferry et al., Arch Biochem. 34:424 (1951).
Marcus E. Carr and Don A. Gabriel, J. Lab. Clin. Med. 96:985-993 (1980).
Marcus E. Carr and Don A. Gabriel, Macromolecules 13:1473-1477 (1980).
Marcus E. Carr et al., Blood 78:482a (1991).

Primary Examiner—Hezron E. Williams
Assistant Examiner—Michael Brook
Attorney, Agent, or Firm—Whitham & Marhoefer

[57] ABSTRACT

The compression elastic modulus of a blood sample is determined by compressing a blood sample (12) between plates (14 and 16) and comparing the voltage signal (32) output from the transducer (22) with a displacement calibration constant $C_d$. The compression elastic modulus is determined on the same sample as the platelet mediated force development.

11 Claims, 3 Drawing Sheets

APPARATUS AND METHOD FOR MEASURING CLOT ELASTIC MODULUS AND FORCE DEVELOPMENT ON THE SAME BLOOD SAMPLE

BACKGROUND OF THE INVENTION

1. Field of the Invention

The present invention generally relates to instrumentation and techniques for monitoring blood clot properties.

2. Description of the Prior Art

The structural and mechanical properties of plasma clots are important for clot integrity and proper hemostasis. In my earlier U.S. Pat. No. 4,986,964, the complete contents of which is herein incorporated by reference, a technique and device was described which directly measures force development during platelet mediated clot retraction. Clot retraction is dependent on intact platelet membrane structure, normal platelet metabolic function, fibrin structure and normal platelet-fibrin interactions. While the physiologic role of clot retraction remains to be fully defined, changes in clot retraction are sensitive to a spectrum of both fluid phase and platelet abnormalities. Force development is completely dependent on platelet function and if platelet function is abnormal or if no platelets are present, force development will be reduced or completely absent.

While force development is dependent on platelet function, the degree of deformation of a blood clot is dependent in large measure on fibrin structure. If the clot structure is very rigid, as sometimes occurs in diseases such as multiple myeloma, clot deformation may be minimal even with large force development. The elastic modulus of a blood clot (gel) is a commonly used measurement of rigidity. For years, clinicians and investigators have been measuring gel elastic modulus as a screen of clot "integrity", meaning a determination of whether the blood possesses the structural characteristics necessary to impede and eventually stop the flow of blood at a site of injury.

There are currently two types of elastic modulus measurements currently being performed on blood clots: tensile (linear stretching) modulus and torsional (twisting) modulus. Tensile modulus measurement techniques for blood clots have been described in Ferry et al., *J. Am. Chem. Soc.* 69:388-400 (1947), Ferry, *Adv. Protein Chem.* 4:1-78 (1948), and Ferry et al., *Arch. Biochem.* 34:424 (1951). Clot tensile modulus measurements have typically been performed on cylindrical clots formed in and subsequently removed from clot forming chambers or vessels. Because manipulation of the clot is required for these types of measurements, there is a chance of inducing irreversible structural changes in the clot and, thereby altering, in unknown ways, the measured elastic modulus. Torsional modulus measurement techniques for blood clots have been described in U.S. Pat. No. 4,317,363 to Shen, and Carr and Shen et al., *Analytical Biochem.* 72:202-211 (1976). Measurement of clot torsional elastic modulus avoids clot manipulation by forming the clot directly within the vessel in which the measurement is made.

Elasticity measurements can be made on a spectrum of specimens ranging from purified solutions to plasma. Unfortunately, the interpretation of elastic modulus variations is difficult in complex systems. Changes in elastic modulus of clots made from purified protein solutions generally reflect changes in fibrin structure. In systems containing cellular elements such as erythrocytes and platelets, changes in elastic modulus may result from fibrin structural alteration or from altered cell function. Since elastic modulus is a complex function of multiple variables, the utility of an isolated elastic modulus measurement is limited. Thus, elastic modulus measurements have not been routinely performed on patient specimens.

SUMMARY OF THE INVENTION

It is therefore an object of the invention to provide instrumentation and a method for making a new elastic modulus measurement on blood samples called the "compression" elastic modulus.

It is another object of the invention to provide an apparatus and technique for using the same blood sample to measure platelet mediated force development and clot compression elastic modulus.

According to the invention, the compression elastic modulus of a blood sample is determined in an apparatus which includes two spaced apart plates, one of which is connected to a transducer. A suitable apparatus is a modified version of the clot retractometer described in U.S. Pat. No. 4,986,964 to Carr, Jr., et al. By monitoring the voltage of the transducer as the two plates are compressed towards one another, as would occur under the influence of a weight, the compression elastic modulus of a blood clot positioned between the plates can be directly measured. The compression elastic modulus of the blood clot is equivalent to the tensile elastic modulus since the pushing effect required for compression elastic modulus measurements would be equal and opposite to the pulling effect required for tensile elastic modulus measurements.

Elastic modulus measurements become much more useful when independent measures of cellular function are available. The clot retractometer described in my U.S. Pat. No. 4,986,964 measures force development during platelet mediated clot retraction and this has been shown to be a novel gauge of platelet function (see, Carr et al., *Blood Coagulation and Fibrinolysis* 2:303-308 (1991), Carr et al., *Am. J. of Med. Sci.* 302:13-18 (1991), and Carr et al., *Blood* 78:482a (1991)). The present invention includes a modification of the clot retractometer described in U.S. Pat. No. 4,986,964 and its operation which allows the direct measurement of clot elastic modulus. Specifically, a weight is placed on the clot retractometer so as to provide a downward force on the top plate acting on the clot and the displacement of the top plate is monitored to determine the compression elastic modulus. Hence, the invention includes an apparatus and method which allows determining platelet function, characterized by force development during clot retraction, and clot structure, characterized by the measured compression elastic modulus, on the same sample. This combination of data allows meaningful interpretation of altered clot structure.

BRIEF DESCRIPTION OF THE DRAWINGS

The foregoing and other objects, aspects and advantages will be better understood from the following detailed description of a preferred embodiment of the invention with reference to the drawings, in which.

DETAILED DESCRIPTION OF THE PREFERRED EMBODIMENTS OF THE INVENTION

The elastic modulus of a material is a measure of the material's rigidity. As shown in Equation 1, elastic modulus (E) is the ratio of stress to strain.

$$E = STRESS/STRAIN \qquad Eq. 1$$

Stress is the force applied to a material. Typically, the force is applied to a specific portion of the material being tested and the units of stress are defined as force per unit area as shown in Equation 2.

$$STRESS = FORCE\ APPLIED/AREA\ OF\ APPLICATION \qquad Eq. 2$$

(units = force/unit area)

Strain, as defined in Equation 3, is the degree of shape change induced by the applied force.

$$STRAIN = PERCENT\ SHAPE\ CHANGE \qquad Eq. 3$$

Figure 1A:
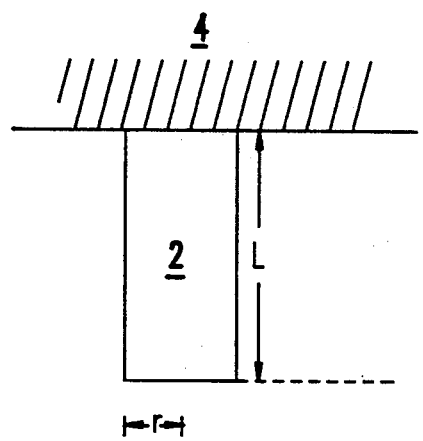
FIGS. 1a and 1b are sequential side views of a blood clot stretching during a traditional tensile elastic modulus measurement.
Figure 1B:
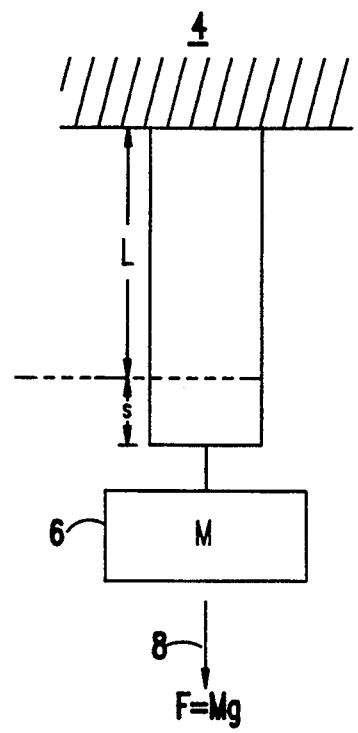

With reference to FIGS. 1a and 1b, linear stretching of a material 2 is used for determining the tensile elastic modulus. FIG. 1a shows that when a material 2 is suspended from a stationary surface 4 it has a length L. FIG. 1b shows that when a weight 6 of mass M is attached to the free end of the material 2, a downward force indicated by arrow 8, which is equivalent to the mass M of weight 6 multiplied by the gravitational constant g, causes the material 2 to stretch a distance s from its original length L. In the case where the material 2 is cylindrical and has radius r, the stress on material 2 caused by the weight 6 according to Equation 2 is calculated as in Equation 4.

$$STRESS = Mg/\pi r^2 \qquad Eq. 4$$

The strain on material 2 caused by the weight 6 can be viewed as the stretching distance s from its original length L. This ignores any reduction in radius of the material 2; however, over small distances L and with large radii r the reduction in radius should be negligible. Therefore, the strain on the material 2 according to Equation 3 is calculated as in Equation 5.

$$STRAIN = s/L \qquad Eq. 5$$

Finally, the tensile elastic modulus E is determined according to Equation 1 according to the calculation of Equation 6.

$$E = (Mg/\pi r^2)/(s/L) \text{ or } MgL/\pi r^2 s \qquad Eq. 6$$

Figure 2:
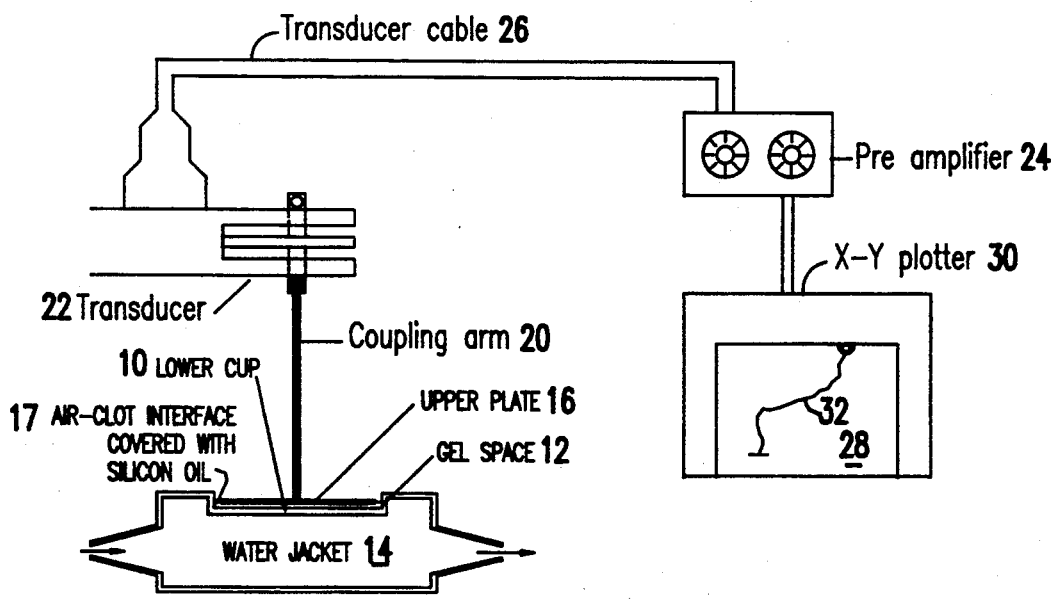
FIG. 2 is a schematic drawing of the clot retractometer instrumentation described U.S. Pat. No. 4,986,964.

FIG. 2 shows a schematic drawing of the clot retractometer instrument described in U.S. Pat. No. 4,986,964. A blood sample 12 is held in a cup 10 which may be thermostatically controlled by a heat transfer media. For example, the temperature of the blood sample 12 can be held constant using a flow through water jacket 14 which includes the cup 10 as a recessed portion. A plate 16 is positioned above the sample 12 and spaced away from the bottom of cup 10. The outer edges of plate 16 are also spaced away from the sides of the cup 10 so that it may move freely towards the bottom. Silicon oil or some other material suitable for reducing evaporation from the clot is preferably placed at the air clot interface 17. The plate 16 is connected to a transducer 22 by a coupling arm 20. The transducer 22 may be a GRASS, Model FT03 strain gauge available from the Grass Instrument Company of Quincy, Mass., or any other suitable device. A transducer cable 26 connects the output from the transducer arm to preamplifier 24 and the amplified signals are output on X-Y plotter 30.

As described in U.S. Pat. No. 4,986,964, platelets within the sample 12 adhere to the bottom of cup 10 and plate 16 and pull plate 16 downward during clot retraction. Movement of plate 16 towards the bottom of the cup 10 causes a change in the output voltage from the transducer 22. The voltage output is recorded as amplified signals 32 on strip paper 28 as a function of time. The output voltage changes linearly with the amount of downward deflection of plate 16. Hence, the downward pulling force caused by the platelets in the sample 12 can be simply determined by comparing the signals 32 output from the sample 12 with signals achieved with different standard calibrating weights suspended from the transducer 22.

Figure 3:
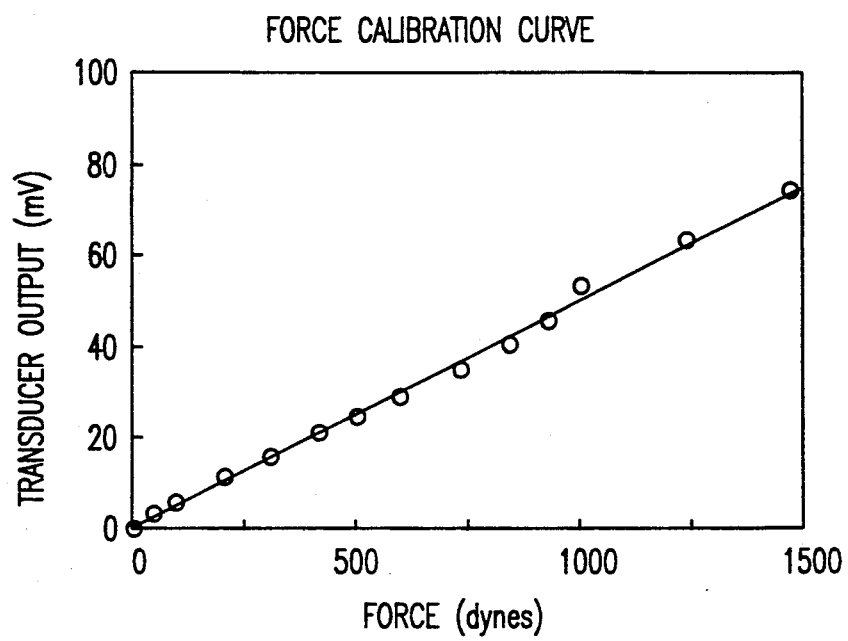
FIG. 3 is a graph showing a force calibration curve of voltage output versus force.

FIG. 3 shows that a calibration curve can be prepared by plotting the mass of different suspended weights versus the voltage output. The slope of the plot is the force calibration constant ($C_f$), which, as shown in Equation 7, preferably has the units of dynes/mV.

$$C_f = FORCE\ APPLIED/VOLTAGE\ GENERATED \qquad Eq. 7$$

(units = dynes/mV)

As described above, when measuring dynamic clot retraction, the voltage development as a function of time is recorded on strip paper 28. These voltages can be converted directly to force measurements by multiplying them by $C_f$. It has been determined that $C_f$ should be determined for each clot since the amount of deflection of plate 16, and thus the voltage output of transducer 22, is dependent on the rigidity of the clot.

Figure 4:
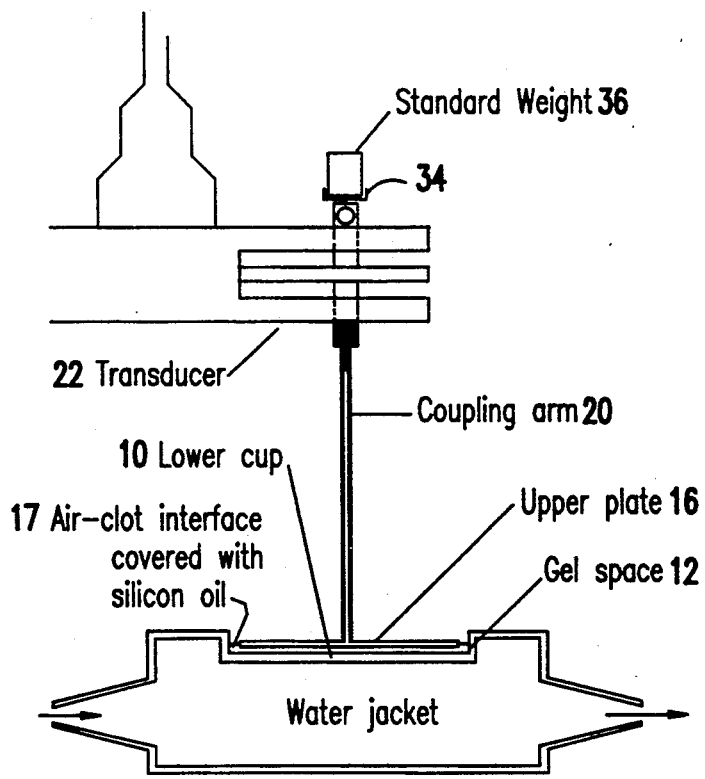
FIG. 4 is an enlarged view of the coupling arm of the clot retractometer of FIG. 2 which shows a modification whereby a standard weight is positioned to exert a downward force on the blood sample.

FIG. 4 shows a slight modification to the clot retractometer of U.S. Pat. No. 4,986,964 which allows the measurement of the "compression" elastic modulus. Specifically, a weight holder 34 is mounted on top of the coupling arm 20 and holds standard weights 36 such that the gravitational force of a weight 36 placed in the holder 34 is exerted down through the coupling arm 20 and plate 16 onto the blood sample (gel or clot) 12 in cup 10. It has been recognized that compressing the blood clot between a pair of plates is analogous to pulling on opposite ends of a blood clot, as is done in traditional tensile elastic modulus measurements, because the force in each case would be equal (i.e., a weight resting on top of a sample exerts the same force on the sample as a weight suspended from the sample). This invention contemplates determining a "compression" elastic modulus of a sample whereby the displacement of the upper plate 16 towards the bottom of the cup 10 represents a reduction in gel width (see Equations 3 and 5 above for explanation of STRAIN).

Figure 5:
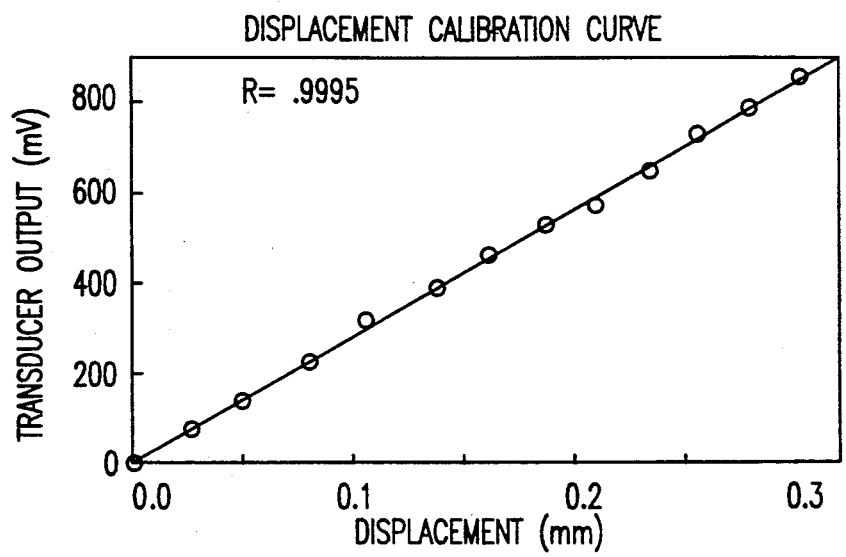
FIG. 5 is a graph showing a displacement calibration curve of voltage output versus displacement of the plate.

Since the transducer 22 is a displacement transducer it can be used to measure the distance the upper plate 16 is moved under the influence of a given force. To measure displacement, the transducer 22 is calibrated by moving the upper plate 16 a series of known distances towards the lower plate 14 and measuring the associated transducer 22 output voltages. FIG. 5 shows a plot of the displacement (in mm) of the plate 16 towards the bottom of the cup 10 versus the voltage output from the transducer 22. The resulting curve is linear and its slope is the displacement calibration constant ($C_d$). As shown in Equation 8, the units of the constant $C_d$ are preferably in mm/mV.

$$C_d = \text{DISTANCE MOVED/VOLTAGE GENERATED} \qquad \text{Eq. 8}$$

(units = mm/mV)

Since $C_d$ is a property of the transducer, it is independent of the sample structure and needs to be calculated only once.

With reference to Equations 9-13 (Equation 9 being identical to Equation 6 above), $C_d$ can be used to calculate the compression elastic modulus of a sample clot as follows:

$$E = (Mg/\pi r^2)/(s/L) \text{ or } MgL/\pi r^2 s \qquad \text{Eq. 9}$$

where M is the mass of the standard weight, g is the gravitational constant of 980 cm/sec$^2$, L is the sample length which in the retractometer is the gap distance between the upper plate 16 and the bottom of cup 10 (in the present retractometer L is 1 mm; however, this distance may vary considerably depending on the needs of the operator), $\pi$ is 3.14159, r is the radius of the upper plate 16 (in the present retractometer r is 18 mm; however, this distance may vary considerably depending on the needs of the operator), and s is the downward deflection of the upper plate 16. As pointed out above, the radius r of the upper plate 16 is preferably large compared to the distance L between the upper plate 16 and the bottom of the cup 10.

Once the displacement calibration curve of FIG. 5 is determined, the downward deflection s of the plate 16 caused by a standard weight 36 being added to holder 34 (see FIG. 4) is calculated according to Equation 10 as follows:

$$s = V_w \cdot C_d \qquad \text{Eq. 10}$$

where $V_w$ is the voltage generated by the standard weight. Equation 11 incorporates the parameters defined for Equations 9 and 10.

$$E = (MgL)/(\pi r^2 V_w C_d) \qquad \text{Eq. 11}$$

Equation 11 can be modified to use a constant K which is dependent on the gap distance and plate radius parameters of the instrument being used, as is set forth in Equations 12 and 13.

$$E = K(M/V_w C_d) \qquad \text{Eq. 12}$$

$$K = (gL/\pi r^2) \qquad \text{Eq. 13}$$

In the present clot retractometer instrument, K is 107.9 mm/(cm*sec$^2$); however, it should be readily apparent that the constant K can vary between instruments.

Hence, from Equations 9-13 it can be seen that a clinician can determine clot compression elastic modulus simply by calibrating the instrument once to get $C_d$, allowing a sample to clot between the upper plate 16 and the bottom of cup 10, then placing a known weight of mass M on the movable plate and recording the voltage output $V_w$. Since the constant K is set by the parameters of the instrument, the compression elastic modulus is calculated according to Equation 12.

Figure 6:
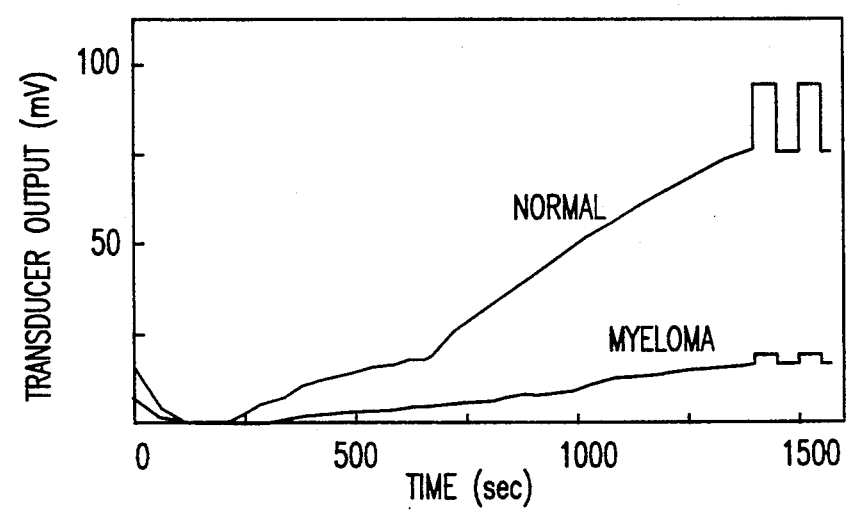
FIG. 6 is a graph showing a plot of unmodified clot retractometer transducer output for two clot retraction experiments involving blood samples from a normal control and a patient with multiple myeloma.

FIG. 6 is an example of data obtained using the clot retractometer of U.S. Pat. No. 4,986,964 which has been modified as shown in FIG. 4. The upper curve was obtained using blood from a normal control patient while the lower curve was obtained using blood from a patient with multiple myeloma. The transducer output is the unmodified voltage developed versus time after the initiation of clotting at time zero. As the clot forms and platelets begin to pull downward on the upper plate 16, voltage is generated. The amount of voltage is proportional to the distance the plate moves. After 1300 seconds into clotting, a standard weight (1 gm) was placed in the weight holder 34 (see FIG. 4) and the weight 36 caused an additional downward displacement of the transducer arm 22. The additional downward displacement is reflected by a spike in voltage output towards the right margin of FIG. 6. A series of step functions are produced when the weight 36 is alternatively applied and removed from the weight holder 34.

Figure 7:
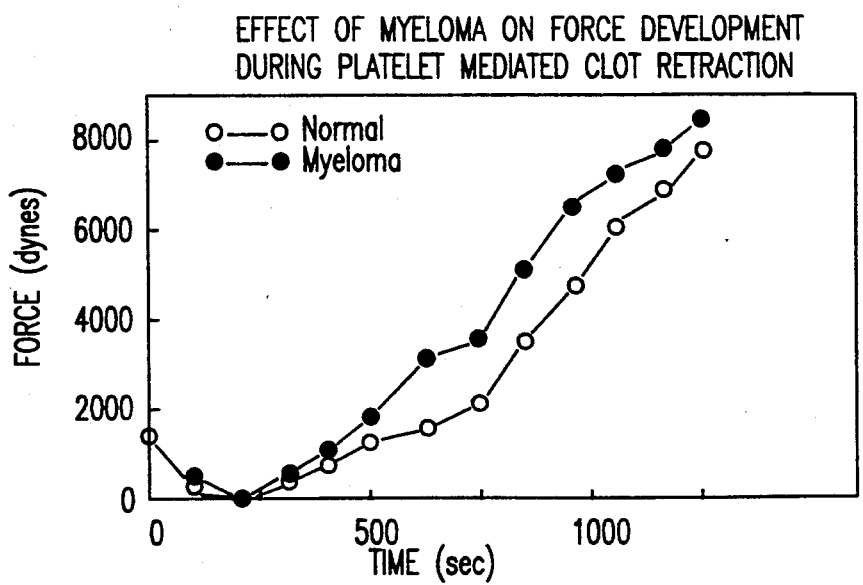
FIG. 7 is a plot of force development during platelet mediated clot retraction for the normal control and the multiple myeloma samples derived directly from the data presented in FIG. 6.

Since the force applied to the transducer 22 is known (e.g., F=mg), the voltage generated allows for the calculation of the force calibration constant and thus conversion of the transducer output signal to force values. FIG. 7 presents the force development data over time which is derived directly from the data of FIG. 6.

Since the displacement calibration curve is invariant with the transducer (see FIG. 5), the voltage step shown in FIG. 6 also allows the direct determination of downward displacement. Specifically, and with reference to Equation 12 above, the difference between transducer output before and after the weight is applied is $V_w$. In FIG. 6, the voltage steps at the right aspect of each curve were generated with the same standard weight (1 gm). Thus, the sample labelled "normal" allowed greater movement of the plate 16, which corresponds to deformation of the clot 12, than the "myeloma" sample even though the force was equal. Hence, the myeloma clot had a higher elastic modulus (i.e., it was stiffer).

Comparing FIGS. 6 and 7 it can be seen that although the transducer output was different for the two samples, conversion to force values revealed that the forces generated by the platelets within the two clots was similar. Hence, the difference between the two signals in FIG. 6 is the result of altered clot elastic modulus.

While the clot compression elastic modulus can be determined using an instrument specifically designed for the task, using the clot retractometer of U.S. Pat. No. 4,986,964 is particularly advantageous because the force development and elastic modulus measurements can be sequentially made on the same blood sample. Measurement of both platelet function, reflected by force development, and clot structure, which is mirrored by elastic modulus, will allow interpretation of altered hemostatic function induced by drugs and various pathologic states. For example, dextran, a commonly utilized intravenous preparation, is known to alter clot structure (see Carr et al., *Macromolecules* 13:1473-1477 (1980), and Carr et al., *J. Lab. Clin. Med.* 96:985-993 (1980)) and may effect platelet function. The essentially simultaneous determination of platelet mediated force development and clot elastic modulus described above in conjunction with FIGS. 6 and 7 allows for the separation and quantification of these effects.

Multiple myeloma, a malignant state characterized by an over production of monoclonal immunoglobulin, is an example of a pathologic state which alters clot structure and which may effect platelet function. Fibrin formed from myeloma plasma is composed of small diameter fibers. Such clots have increased elastic modulus and decreased gel pore size. Clot retraction as measured by the commonly used technique of serum expression is virtually absent in such cases. In the past, this has been interpreted as an anti-platelet effect. However, my technique of simultaneous measurement of force development and elastic modulus demonstrates that platelet function is only minimally effected while the elastic modulus is significantly altered (FIG. 6). Hence, this combination of data allows separation of the altered clot structure from the altered platelet function, thereby allowing appropriate interpretation. With reference to FIG. 4, this is accomplished by first monitoring clot retraction in the clot retractometer and subsequently placing a weight 36 in a position which exerts a downward force on the upper plate 16 while monitoring the displacement of the upper plate as the clot is compressed. The standard weight 36 produces a known force on the clot contained in the cup. The transducer voltage output simultaneously verifies the voltage to force calibration curve and yields the amount of upper plate displacement from the predetermined voltage to displacement curve. The ratio of force to displacement is a direct measure of elastic modulus.

As discussed in detail in U.S. Pat. No. 4,986,964, plasma clot structure is sensitive to the microenvironment in which it forms. Shifts in ionic strength, divalent ion concentration, pH, fibrinogen concentration, and clotting enzyme concentration will alter the rate of fibrin assembly and the structure of the eventual clot. Reproducible measurements of plasma clot characteristics are only possible if these conditions are standardized and held constant. The preferred microenvironmental conditions for the blood sample are approximately pH 7.4, ionic strength of approximately 1.0 to 2.0, and calcium concentration ranging from 5 mM to 20 mM. In addition, temperature plays an important role in the clotting response and optimum results are achieved when the blood sample is maintained at a temperature ranging from 35° C. to 38° C.

While the invention has been described in terms of its preferred embodiments, those skilled in the art will recognize that the invention can be practiced with modification within the spirit and scope of the appended claims.

Having thus described my invention, what I claim as new and desire to secure by Letters Patent is as follows:

1. An apparatus for analyzing blood and plasma samples, comprising both a means for analyzing platelet function and a means for analyzing clot structure for the same sample, wherein both said means for analyzing platelet function and said means for analyzing clot structure for the same sample utilize a common pair of spaced apart plates wherein a first plate of said pair of spaced apart plates is connected to a displacement sensor which monitors movement of said first plates towards a second plate of said spaced apart plates.

2. An apparatus as recited in claim 1 wherein said means for analyzing platelet function provides a measurement of platelet mediated force development.

3. An apparatus as recited in claim 1 wherein said means for analyzing clot structure provides a measurement of clot elastic modulus.

4. An apparatus as recited in claim 1 further comprising a means for applying a known amount of force on said first plate which biases said first plate toward said second plate and a means for determining an amount of movement of said first plate towards said second plate caused by said known amount of force.

5. A method of determining an elastic modulus of a blood sample, comprising the steps of:
positioning a blood sample between a pair of spaced apart plates;
compressing said blood sample between said pair of spaced apart plates;
monitoring electrical output from a sensor connected to one of said pair of spaced apart plates during said compressing step; and
calculating an elastic modulus of said blood sample based on a relationship between said electrical output and a degree of compression exerted during said compressing step.

6. A method as recited in claim 5 wherein said step of compressing includes the step of providing a weight of known mass at a position where gravitational forces acting on said weight will be transferred to one of said pair of spaced apart plates.

7. A method as recited in claim 5 wherein said step of calculating includes the step of determining a displacement calibration constant for said sensor.

8. A method of determining the retraction force and elastic modulus characteristics of a single blood sample, comprising the steps of
positioning a blood sample between a pair of spaced apart plates, the spacing allowing platelets in said blood sample to adhere to both of said plates;
monitoring a pulling force exerted on one of said plates pulling said plates towards each other while said blood sample is clotting;
determining a retraction force from measurements made during said monitoring step;
compressing said blood sample between said pair of spaced apart plates;
monitoring electrical output from a sensor connected to one of said pair of spaced apart plates during said compressing step; and
calculating an elastic modulus of said blood sample based on a relationship between said electrical output and a degree of compression exerted during said compressing step.

9. A method as recited in claim 8 further comprising the step of maintaining the blood sample between 35° C. and 38° C. during said step of monitoring said pulling force.

10. A method as recited in claim 8 wherein said retraction force and said elastic modulus are determined at approximately the same time.

11. An apparatus for determining the retraction force and elastic modulus characteristics of a blood sample, comprising:
- a pair of spaced apart plates wherein the spacing allows platelets in a blood sample to adhere to both of said pair of spaced apart plates;
- one or more sensors connected to at least one of said pair of spaced apart plates, said one or more sensors providing electrical output signals which are a function of a force exerted to move said spaced apart plates towards each other;
- a means for monitoring a pulling force exerted by a clotting blood sample between said pair of spaced apart plates, said pulling force being indicative of platelet mediated force development;
- a means for compressing a blood sample between said pair of spaced apart plates;
- a means for monitoring a degree of compressive movement of said pair of spaced apart plates towards one another exerted by said means for compressing said blood sample, said degree of compressive movement being indicative of clot elastic modulus; and
- a means for providing information related to platelet function and clot structure based on said platelet mediated force development and said clot elastic modulus.

* * * * *